United States Patent
He et al.

(10) Patent No.: US 7,416,855 B2
(45) Date of Patent: *Aug. 26, 2008

(54) IMMUNOASSAY METHODS FOR DETECTING INTERLEUKIN-1 β CONVERTING ENZYME LIKE APOPTOSIS PROTEASE-3

(75) Inventors: Wei-Wu He, Columbia, MD (US); Craig A. Rosen, Laytonsville, MD (US); Peter L. Hudson, Germantown, MD (US); Gregg A. Hastings, Westlake Village, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 358 days.

This patent is subject to a terminal disclaimer.

(21) Appl. No.: 10/801,669

(22) Filed: Mar. 17, 2004

(65) Prior Publication Data
US 2004/0171059 A1    Sep. 2, 2004

Related U.S. Application Data

(60) Division of application No. 09/613,508, filed on Jul. 10, 2000, now Pat. No. 6,835,555, which is a division of application No. 08/462,969, filed on Jun. 5, 1995, now Pat. No. 6,087,150, which is a continuation-in-part of application No. 08/334,251, filed on Nov. 1, 1994, now Pat. No. 6,538,121.

(51) Int. Cl.
G01N 33/00 (2006.01)
G01N 33/53 (2006.01)
C12N 5/16 (2006.01)

(52) U.S. Cl. ............. 435/7.92; 435/7.1; 435/7.93; 435/7.94; 435/7.95; 435/326; 436/518; 436/540

(58) Field of Classification Search ............ None
See application file for complete search history.

(56) References Cited

U.S. PATENT DOCUMENTS

| 5,552,536 | A | 9/1996 | Nicholson et al. |
| 6,733,981 | B2 * | 5/2004 | He et al. .......... 435/7.1 |
| 6,835,555 | B1 | 12/2004 | He et al. |

FOREIGN PATENT DOCUMENTS

| CA | 2075662 | 2/1993 |
| EP | 0 533 226 A2 | 3/1993 |
| WO | WO-96/33268 | 10/1996 |

OTHER PUBLICATIONS

Bast et al. "Translational Crossroads for Biomarkers" Clin Canser Res 2005; 11(17), 6103-6108.*
LaBaer et al. "So, You Want to Look for Biomarkers" Journal of Proteome Research 2005; 4, 1053-1059.*
Baker "In Biomarkers We Trust?" Nature Biotechnology 2005; 23(3), 297-304.*
Fernandes-Alnemri et al. ("Mch3, a Novel Human Apoptotic Cysteine Protease Highly Related to CPP32" Cancer Research 55 (1995), 6045-6052).*
iHOP (Information Hyperlinked over Proteins), entry for CASP7, downloaded from http://www.ihop-net.org/UniPub/iHOP/gs/86932.html on Feb. 13, 2007.*
Harlow, E. and Lane, D., Antibodies: A Laboratory Manual (1988) Cold Spring Harbor Laboratory Press, Cold Spring Harbor, NY, pp. 23-26, 321-323, 584-585, and 591-592.*
GeneSeq Accession No. T66992 (Aug. 5, 1997) Idun Pharm., Inc. et al., "Apotic protease Mch3-alpha cDNA".
GeneSeq Accession No. T66970 (Jul. 21, 1997) Vertex Pharm., Inc., "Cysteine protease CMH-1 cDNA".
GeneSeq Accession No. T66993 (Aug. 5, 1997) Idun Pharm., Inc., "Cysteine protease Mch3-beta cDNA".
GeneSeq Accession No. W15247 (Jul. 21, 1997) Vertex Pharm., Inc, "Cysteine protease CMH-1".
GeneSeq Accession No. W15262 (Aug. 5, 1997) Idun Pharm., Inc., "Apotic protease Mch3-alpha".
GeneSeq Accession No. W15263 (Aug. 5, 1997) Idun Pharm., Inc., "Cysteine protease Mch3-beta".
GenBank Accession No. U39613 (Jan. 19, 1996) Duan et al., "Human cysteine protease ICE-LAP3 mRNA".
GenBank Accession No. U37448 (Dec. 14, 1995) Pernandes-Alnemri et al., "Human Mch3 isoform alpha (Mch3) mRNA".
GenBank Accession No. U40281 (Jan. 27, 1996) Lippke et al., "Human cysteine protease CMH-1 mRNA".
GenBank Accession No. U67319 (Mar. 19, 1997) Juan et al., "Human Lice2 beta cysteine protease mRNA".
GenBank Accession No. U67320 (Mar. 19, 1997) Juan et al., "Human Lice2 gamma cysteine protease mRNA".
GenBank Accession No. U37449 (Dec. 14, 1995) Fernandes-Alnemri et al., "Human Mch3 isoform beta (Mch3) mRNA".
GenBank Accession No. H91868 (Nov. 29, 1995) Hillier et al., "ys81a06.r1 Soares retina N2b4HR *Homo sapiens* cDNA clone Image:221170 5' similar to SP:A49429 A49429 CED-3+Interleukin-1 Beta-Converting Enzyme Homolog—Caenorhabditis;, mRNA sequence".
GeneSeq Accession No. V05471 (Jul. 2, 1998) Univ. Michigan, "Nucleic acid encoding a protein designated Yama".
GeneSeq Accession No. T33567 (Dec. 6, 1996) Univ. Michigan, "Pro-Yama cDNA".

(Continued)

*Primary Examiner*—Long V. Le
*Assistant Examiner*—Christine E. Foster

(57) ABSTRACT

Disclosed are human interleukin-1 β converting enzyme like apoptosis proteases-3 and 4 and DNA (RNA) encoding such polypeptides. Also provided is a procedure for producing such polypeptides by recombinant techniques and antibodies and antagonists against such polypeptides. Also provided are methods of using the polypeptides, for example, as an anti-tumor agent, and antiviral agent, and antibodies and antagonists against such polypeptides for example, for treating Alzheimer's disease, Parkinson's disease, rheumatoid arthritis and head injury. Diagnostic assays for identifying mutations in nucleic acid sequence encoding a polypeptide of the present invention and for detecting altered levels of the polypeptide of the present invention for detecting diseases are also disclosed.

12 Claims, 7 Drawing Sheets

OTHER PUBLICATIONS

GeneSeq Accession No. V32608 (Oct. 26, 1998) Merck Frosst Canada, Inc., "Mutant human apopain (caspase-3) pro-enzyme cDNA".

GeneSeq Accession No. V32615 (Oct. 26, 1998) Merck Frosst Canada, Inc., "Mutant human apopain (caspase-3) pro-enzyme cDNA".

GeneSeq Accession No. W00677 (Dec. 6, 1996) Univ. Michigan, "Pro-Yama".

GeneSeq Accession No. W00372 (Jun. 26, 1997) Merck & Co., Inc. et al., "Apopain CPP32beta proenzyme".

GeneSeq Accession No. W41688 (Jul. 2, 1998) Univ. Michigan, "Amino acid sequence of a protein designated Yama".

GeneSeq Accession No. W16600 (Jun. 26, 1997) Merck & Co., Inc. et al., "Apopain CPP32a proenzyme".

GeneSeq Accession No. W48945 (Oct. 26, 1998) Merck Frosst Canada, Inc., "Mutant human apopain (caspase-3) C163S pro-enzyme".

GeneSeq Accession No. W48937 (Oct. 26, 1998) Merck Frosst Canada, Inc., "Mutant human apopain (caspase-3) C163S pro-enzyme".

GenBank Accession No. U26943 (Aug. 29, 1995) Tewari et al., "Human cysteine protease Yama mRNA".

GenBank Accession No. U13737 (Apr. 14, 1995) Fernandes-Alnemri et al., "Human cysteine protease CPP32 isoform alpha mRNA".

GenBank Accession No. U13738 (Apr. 14, 1995) Fernandes-Alnemri et al., "Human cysteine protease CPP32 isoform beta mRNA".

GenBank Accession No. T10341 (Jun. 7, 1994) Soares et al., "seq1254 b4HB3MA Cot8-HAP-Ft *Homo sapiens* cDNA clone b4HB3MA-COT8-HAP-Ft280 5' similar to similar Human Cysteine proteinase and to Mouse interleukin 1-beta convertase, mRNA sequence".

GenBank Accession No. H29199 (Jul. 17, 1995) Hillier et al., "ym31f11.r1 Soares infant brain 1NIB *Homo sapiens* cDNA clone Image:49729 5' similar to SP:A49429 A49429 CED-3=Interleukin-1 Beta-Converting Enzyme Homolog—Caenorhabditis;, mRNA sequence".

GenBank Accession No. N85243 (Apr. 1, 1996) Liew, C.C., J2957F Human fetal heart, Lambda ZAP Express *Homo sapiens* cDNA clone J2957 5' similar to Cysteine Protease CPP32, mRNA sequence.

Cerretti et al., "Molecular Cloning of the Interleukin-1β Converting Enzyme," Science, 256:97-100 (Apr. 3, 1992).

Walker et al., "Crystal Structure of the Cysteine Protease Interleukin-1β-Converting Enzyme: A (p20/p10)2 Homodimer," Cell, 78:343-352 (Jul. 29, 1994), Cell Press.

Wang et al., "Ich-1, an Ice/ced-3-Related Gene, Encodes Both Positive and Negative Regulators of Programmed Cell Death," Cell, 78:739-750 (Sep. 9, 1994), Cell Press.

Henkart, P., "ICE Family Proteases: Mediators of All Apoptotic Cell Death?," Immunity, 4:195-201 (Mar. 1996), Cell Press.

Kamens et al., "Identification and Characterization of ICH-2, a Novel Member of the Interleukin-1β-converting Enzyme Family of Cysteine Proteases," J. Biol. Chem., 270(25):15250-15256 (1995), The American Society for Biochemistry and Molecular Biology, Inc., U.S.A.

Munday et al., "Molecular Cloning and Pro-apoptotic Activity of ICErelII and ICErelIII, Members of the ICE/CED-3 Family of Cysteine Proteases," J. Biol. Chem., 270(26):15870-15876 (1995), The American Society for Biochemistry and Molecular Biology, Inc., U.S.A.

Tewari et al., "Yama/CPP32β, a Mammalian Homolog of CED-3, Is a CrmA-Inhibitable Protease That Cleaves the Death Substrate Poly(ADP-Ribose) Polymerase," Cell, 81:801-809 (1995), Cell Press.

Faucheu et al., "A novel human protease similar to the interleukin-1β converting enzyme induces apoptosis in transfected cells," The EMBO Journal, 14(9):1914-1922 (1995).

Greenfeder et al., "Molecular Cloning and Characterization of a Second Subunit of the Interleukin 1 Receptor Complex," J. Biol. Chem., 270(23):13757-13765 (Jun. 9, 1995), The American Society for Biochemistry and Molecular Biology, Inc., U.S.A.

Miura et al., "Induction of Apoptosis in Fibroblasts by IL-1β-Converting Enzyme, a Mammalian Homolog of the C. elegans Cell Death Gene ced-3," Cell, 75:653-660 (Nov. 19, 1993), Cell Press.

Fernandes-Alnemri et al., "CPP32, a Novel Human Apoptotic Protein with Homology to Caenorhabditis elegans Cell Death Protein Ced-3 and Mammalian Interleukin-1β-converting Enzyme," J. Biol. Chem., 269(49):30761-30764, (Dec. 9, 1994), The American Society for Biochemistry and Molecular Biology, Inc., U.S.A.

Ellis et al., "Mechanisms and Functions of Cell Death," Annu. Rev. Cell Biol., 7:663-698 (1991), Annual Reviews Inc.

Barinaga M., "Cell Suicide: By Ice, Not Fire," Science, 263:754-756 (Feb. 11, 1994).

Callard et al., "The Cytokine Facts Book," New York: Academic Press (1994), p. 31.

* cited by examiner

FIGURE 1A

```
  1 GCACGAGAAACTTTGCTGTGCGCGTTCTCCCGCGCGCGGGCTCAACTTTGTAGAGCGAGG    60

61 GGCCAACTTGGCAGAGCGCGCGGCCAGCTTTGCAGAGAGCGCCCTCCAGGGACTATGCGT   120

121 GCGGGGACACGGGTCGCTTTGGGCTCTTCCACCCCTGCGGAGCGCACTACCCCGAGCCAG   180

181 GGGCGGTGCAAGCCCCGCCCGGCCCTACCCAGGGCGGCTCCTCCCTCCGCAGCGCCGAGA   240

241 CTTTTAGTTTCGCTTTCGCTAAAGGGGCCCCAGACCCTTGCTGCGGAGCGACGGAGAGAG   300

301 ACTGTGCCAGTCCCAGCCGCCCTACCGCCGTGGGAACGATGGCAGATGATCAGGGCTGTA   360
  1                                      M  A  D  D  Q  G  C  I     8

361 TTGAAGAGCAGGGGGTTGAGGATTCAGCAAATGAAGATTCAGTGGATGCTAAGCCAGACC   420
  9  E  E  Q  G  V  E  D  S  A  N  E  D  S  V  D  A  K  P  D  R    28

421 GGTCCTCGTTTGTACCGTCCCTCTTCAGTAAGAAGAAGAAAAATGTCACCATGCGATCCA   480
 29  S  S  F  V  P  S  L  F  S  K  K  K  K  N  V  T  M  R  S  I    48

481 TCAAGACCACCCGGGACCGAGTGCCTACATATCAGTACAACATGAATTTTGAAAAGCTGG   540
 49  K  T  T  R  D  R  V  P  T  Y  Q  Y  N  M  N  F  E  K  L  G    68

541 GCAAATGCATCATAATAAACAACAAGAACTTTGATAAAGTGACAGGTATGGGCGTTCGAA   600
 69  K  C  I  I  I  N  N  K  N  F  D  K  V  T  G  M  G  V  R  N    88

601 ACGGAACAGACAAAGATGCCGAGGCGCTCTTCAAGTGCTTCCGAAGCCTGGGTTTTGACG   660
 89  G  T  D  K  D  A  E  A  L  F  K  C  F  R  S  L  G  F  D  V   108

661 TGATTGTCTATAATGACTGCTCTTGTGCCAAGATGCAAGATCTGCTTAAAAAAGCTTCTG   720
109  I  V  Y  N  D  C  S  C  A  K  M  Q  D  L  L  K  K  A  S  E   128

721 AAGAGGACCATACAAATGCCGCCTGCTTCGCCTGCATCCTCTTAAGCCATGGAGAAGAA   780
129  E  D  H  T  N  A  A  C  F  A  C  I  L  L  S  H  G  E  E  N   148

781 ATGTAATTTATGGGAAAGATGGTGTCACACCAATAAAGGATTTGACAGCCCACTTTAGGG   840
149  V  I  Y  G  K  D  G  V  T  P  I  K  D  L  T  A  H  F  R  G   168

841 GGGATAGATGCAAAACCCTTTTAGAGAAACCCAAACTCTTCTTCATTCAGGCTTGCCGAG   900
169  D  R  C  K  T  L  L  E  K  P  K  L  F  F  I  Q  A  C  R  G   188

901 GGACCGAGCTTGATGATGCCATCCAGGCCGACTCGGGGCCCATCAATGACACAGATGCTA   960
189  T  E  L  D  D  A  I  Q  A  D  S  G  P  I  N  D  T  D  A  N   208
```

FIGURE 1B

```
961  ATCCTCGATACAAGATCCCAGTGGAAGCTGACTTCCTCTTCGCCTATTCCACGGTTCCAG  1020
209    P  R  Y  K  I  P  V  E  A  D  F  L  F  A  Y  S  T  V  P  G   228

1021 GCTATTACTCGTGGAGGAGCCCAGGAAGAGGCTCCTGGTTTGTGCAAGCCCTCTGCTCCA  1080
229    Y  Y  S  W  R  S  P  G  R  G  S  W  F  V  Q  A  L  C  S  I   248

1081 TCCTGGAGGAGCACGGAAAAGACCTGGAAATCATGCAGATCCTCACCAGGGTGAATGACA  1140
249    L  E  E  H  G  K  D  L  E  I  M  Q  I  L  T  R  V  N  D  R   268

1141 GAGTTGCCAGGCACTTTGAGTCTCAGTCTGATGACCCACACTTCCATGAGAAGAAGCAGA  1200
269    V  A  R  H  F  E  S  Q  S  D  D  P  H  F  H  E  K  K  Q  I   288

1201 TCCCCTGTGTGGTCTCCATGCTCACCAAGGAACTCTACTTCAGTCAATAGCCATATCAGG  1260
289    P  C  V  V  S  M  L  T  K  E  L  Y  F  S  Q                   303

1261 GGTACATTCTAGCTGAGAAGCAATGGGTCACTCATTAATGAATCACATTTTTTTATGCTC  1320

1321 TTGAAATATTCAGAAATTCTCCAGGATTTTAATTTCAGGAAAATGTATT  1369
```

FIGURE 2A

```
  1 GCACGAGCGGATGGGTGCTATTGTGAGGCGGTTGTAGAAGAGTTTCGTGAGTGCTCGCAG 60

61 CTCATACCTGTGGCTGTGTATCCGTGGCCACAGCTGGTTGGCGTCGCCTTGAAATCCCAG 120

121 GCCGTGAGGAGTTAGCGAGCCCTGCTCACACTCGGCGCTCTGGTTTTCGGTGGGTGTGCC 180

181 CTGCACCTGCCTCTTCCCGCATTCTCATTAATAAAGGTATCCATGGAGAACACTGAAAAC 240
  1                                           M  E  N  T  E  N    6

241 TCAGTGGATTCAAAATCCATTAAAAATTTGGAACCAAAGATCATACATGGAAGCGAATCA 300
  7  S  V  D  S  K  S  I  K  N  L  E  P  K  I  I  H  G  S  E  S  26

301 ATGGACTCTGGAATATCCCTGGACAACAGTTATAAAATGGATTATCCTGAGATGGGTTTA 360
 27  M  D  S  G  I  S  L  D  N  S  Y  K  M  D  Y  P  E  M  G  L  46

361 TGTATAATAATTAATAATAAGAATTTTCATAAAAGCACTGGAATGACATCTCGGTCTGGT 420
 47  C  I  I  I  N  N  K  N  F  H  K  S  T  G  M  T  S  R  S  G  66

421 ACAGATGTCGATGCAGCAAACCTCAGGGAAACATTCAGAAACTTGAAATATGAAGTCAGG 480
 67  T  D  V  D  A  A  N  L  R  E  T  F  R  N  L  K  Y  E  V  R  86

481 AATAAAAATGATCTTACACGTGAAGAAATTGTGGAATTGATGCGTGATGTTTCTAAAGAA 540
 87  N  K  N  D  L  T  R  E  E  I  V  E  L  M  R  D  V  S  K  E  106

541 GATCACAGCAAAAGGAGCAGTTTTGTTTGTGTGCTTCTGAGCCATGGTGAAGAAGGAATA 600
107  D  H  S  K  R  S  S  F  V  C  V  L  L  S  H  G  E  E  G  I  126

601 ATTTTTGGAACAAATGGACCTGTTGACCTGAAAAAAATAACAAACTTTTTCAGAGGGGAT 660
127  I  F  G  T  N  G  P  V  D  L  K  K  I  T  N  F  F  R  G  D  146

661 CGTTGTAGAAGTCTAACTGGAAAACCCAAACTTTTCATTATTCAGGCCTGCCGTGGTACA 720
147  R  C  R  S  L  T  G  K  P  K  L  F  I  I  Q  A  C  R  G  T  166

721 GAACTGGACTGTGGCATTGAGACAGACAGTGGTGTTGATGATGACATGGCGTGTCATAAA 780
167  E  L  D  C  G  I  E  T  D  S  G  V  D  D  D  M  A  C  H  K  186

781 ATACCAGTGGAGGCCGACTTCTTGTATGCATACTCCACAGCACCTGGTTATTATTCTTGG 840
187  I  P  V  E  A  D  F  L  Y  A  Y  S  T  A  P  G  Y  Y  S  W  206
```

FIGURE 2B

```
 841 CGAAATTCAAAGGATGGCTCCTGGTTCATCCAGTCGCTTTGTGCCATGCTGAAACAGTAT  900
 207  R   N   S   K   D   G   S   W   F   I   Q   S   L   C   A   M   L   K   Q   Y   226

901 GCCGACAAGCTTGAATTTATGCACATTCTTACCCGGGTTAACCGAAAGGTGGCAACAGAA  960
 227  A   D   K   L   E   F   M   H   I   L   T   R   V   N   R   K   V   A   T   E   246

961 TTTGAGTCCTTTTCCTTTGACGCTACTTTTCATGCAAAGAAACAGATTCCATGTATTGTT 1020
 247  F   E   S   F   S   F   D   A   T   F   H   A   K   K   Q   I   P   C   I   V   266

1021 TCCATGCTCACAAAAGAACTCTATTTTTATCACTAAAGAAATGGTTGGTTGGTGGTTTTT 1080
 267  S   M   L   T   K   E   L   Y   F   Y   H   *                                      277

1081 TTTAGTTTGTATGCCAAGTGAGAAGATGGTATATTTGGGTACTGTATTTCCCTCTCATTG 1140

1141 GGGACCTACTCTCATGCTG 1159
```

FIGURE 3B

```
              210                 220                 230                 240
 58  - - - - - - - - - - - - - - - - - Y Q Y N - - - M N F E K L - - - - - - - - -            ICE-LAP-3
 37  - - - - - - - - - - - - - - - - - - - Y K - - - M D Y P E M - - - - - - - - -            ICE-LAP-4
122  - - - A M P T S S G S - - - - - E G N V K L C S L E E A Q R I W K Q K S A E I            Human ICE
197  R N R S F S K A S G P T Q Y I F H E E D M N F V D A P T I S R V F D E K T - - M          CED-3

250                 260                 270                 280
 68  - - - - - - - - - - - G K C I I I N N K N F D K V T G M G V R N G T D K D A E A L        ICE-LAP-3
 45  - - - - - - - - - - - G L C I I I N N K N F H K S T G M T S R S G T D V D A A N L        ICE-LAP-4
153  - Y P I M D K S S R T R L A L I I C N E E F D - - S I P R R T G A E V D I T G M          Human ICE
235  Y R N F - - S S P R G M C L I I N E H F E Q - - M P T R N G T K A D K D N L              CED-3

290                 300                 310                 320
 98  F K C F R S L G F D V I V Y N D C S C A K M Q D L L K K A S E - - E D H T N A A          ICE-LAP-3
 75  R E T F R N L K Y E V R N K N D L T R E E I V E L M R D V S K - - E D H S K R S          ICE-LAP-4
190  T M L L Q N L G Y S V D V K K N L T A S D M T T E L E A F A H R P E H K T S D S          Human ICE
270  N L F R C M G Y T V I C K D N L T G R G M L L T I R D F A K - - H E S H G D S            CED-3

330                 340                 350                 360
136  C F A C I L L S H G E E N V I Y G K - - - D G - V - - T P I K D L T A H F R G D          ICE-LAP-3
113  S F V C V L L S H G E E G I I F G T - - - N G - P - - V D L K K I T N F F R G D          ICE-LAP-4
230  T F L - V F M S H G I R E G I C G K K H S E Q V P D I L Q L N A I F N M L N T K          Human ICE
308  A I L - V I L S H G E E N V I G V - - E D I P - - I S T H E I Y D L N A A                CED-3

370                 380                 390                 400
170  R C K T L L E K P K L F F I Q A C R G T E L D D A I Q A D S G P I N - - - - -            ICE-LAP-3
147  R C R S L T G K P K L F I I Q A C R G T E L D C G I E T D S G V D D - - - - -            ICE-LAP-4
269  N C P S L K D K P K V I I I Q A C R G D - - S P G V V W F K D S V G S G N L S            Human ICE
342  N A P R L A N K P K I V F V Q A C R G E R R D N G F P P V L D S V D G V P A F L R        CED-3
```

FIGURE 3C

```
                                410                 420                430                  440
     204  - - - D T D A N   P R Y - - - - - - - - - - - K I P V E A D F L   F A Y S T       ICE-LAP-3
     181  - - - D M A C H - - - - - - - - - - - - - - K I P V E A D F L   Y A Y S T         ICE-LAP-4
     307  - - - L P T T E E   F E - - - - - - D D A I K   K A H I E K D F   I A F C   S S   Human ICE
     382  R G W D N R D G   P L F N F L G C V R P Q V Q Q V W R   K K P S Q A D I L   I A Y A T  CED-3

450                 460                470                  480
     226  V P G K   Y S W R   S P G   R G S W F   V Q A L C   S I L E E H G K D L   E I M Q   I L T R V  ICE-LAP-3
     200  A P G K   Y S W R N S   K D G S W F I Q   S L C A M L K Q Y   A D K   L E F M H   I L T R V  ICE-LAP-4
     334  T P D N   V S W R   H P T M   G S   V F I G R   L I E H M Q   E Y A C S C   D V E E I   F - - -  Human ICE
     422  T A Q Y V S W R N S   A R G S M H I Q A   V C E V F S T   H A K D   M D V E L L T E V       CED-3

490                 500                510                  520
     266  N D R   V A R H   F E S   Q S D D P H   F H E K K Q I P C   V V S M L T K E L Y F   - - -  ICE-LAP-3
     240  N R K   V A T E F E S   F S F D A T F H A K K Q I P C   I V S M L T K E L Y F   - - -   ICE-LAP-4
     371  - R K   V A   R F S   F E Q P D   G R A Q M P T T E R V T - - - L T   R C F Y L   F P G H   Human ICE
     462  N K K   V A C G F Q T S Q   G S N I L - - - K Q M P E M T S R L L K F Y F   W P E A       CED-3

302  - - - S Q .                                                                  ICE-LAP-3
     276  - - - Y H .                                                                  ICE-LAP-4
     404  R N S A V                                                                    Human ICE
     499                                                                                CED-3
```

Decoration 'Decoration #1': Shade (with solid black) residues that match the Consensus exactly.

SEQUENCE LISTING

<160> NUMBER OF SEQ ID NOS: 14

<210> SEQ ID NO 1
<211> LENGTH: 1369
<212> TYPE: DNA
<213> ORGANISM: Homo sapiens

<400> SEQUENCE: 1

```
gcacgagaaa ctttgctgtg cgcgttctcc cgcgcgcggg ctcaactttg tagagcgagg      60
ggccaacttg gcagagcgcg cggccagctt tgcagagagc gccctccagg gactatgcgt     120
gcggggacac gggtcgcttt gggctcttcc accctgcgg agcgcactac cccgagccag     180
gggcggtgca agccccgccc ggccctaccc agggcggctc ctccctccgc agcgccgaga     240
cttttagttt cgctttcgct aaagggggccc cagacccttg ctgcggagcg acggagagag     300
actgtgccag tcccagccgc cctaccgccg tgggaacgat ggcagatgat cagggctgta     360
ttgaagagca gggggttgag gattcagcaa atgaagattc agtggatgct aagccagacc     420
ggtcctcgtt tgtaccgtcc ctcttcagta agaagaagaa aaatgtcacc atgcgatcca     480
tcaagaccac ccgggaccga gtgcctacat atcagtacaa catgaatttt gaaaagctgg     540
gcaaatgcat cataataaac aacaagaact ttgataaagt gacaggtatg ggcgttcgaa     600
acggaacaga caaagatgcc gaggcgctct tcaagtgctt ccgaagcctg ggttttgacg     660
```

```
tgattgtcta taatgactgc tcttgtgcca agatgcaaga tctgcttaaa aaagcttctg    720
aagaggacca tacaaatgcc gcctgcttcg cctgcatcct cttaagccat ggagaagaaa    780
atgtaattta tgggaaagat ggtgtcacac aataaagga tttgacagcc cactttaggg    840
gggatagatg caaacccctt ttagagaaac ccaaactctt cttcattcag gcttgccgag    900
ggaccgagct tgatgatgcc atccaggccg actcggggcc catcaatgac acagatgcta    960
atcctcgata caagatccca gtggaagctg acttcctctt cgcctattcc acggttccag   1020
gctattactc gtggaggagc ccaggaagag gctcctggtt tgtgcaagcc ctctgctcca   1080
tcctggagga gcacggaaaa gacctggaaa tcatgcagat cctcaccagg gtgaatgaca   1140
gagttgccag gcactttgag tctcagtctg atgacccaca cttccatgag aagaagcaga   1200 tccctgtgt ggtctccatg ctcaccaagg aactctactt cagtcaatag ccatatcagg    1260
ggtacattct agctgagaag caatgggtca ctcattaatg aatcacattt ttttatgctc   1320
ttgaaatatt cagaaattct ccaggatttt aatttcagga aaatgtatt                1369
```

<210> SEQ ID NO 2
<211> LENGTH: 303
<212> TYPE: PRT
<213> ORGANISM: Homo sapiens

<400> SEQUENCE: 2

```
Met Ala Asp Asp Gln Gly Cys Ile Glu Glu Gln Gly Val Glu Asp Ser
1               5                   10                  15

Ala Asn Glu Asp Ser Val Asp Ala Lys Pro Asp Arg Ser Ser Phe Val
            20                  25                  30

Pro Ser Leu Phe Ser Lys Lys Lys Asn Val Thr Met Arg Ser Ile
        35                  40                  45

Lys Thr Thr Arg Asp Arg Val Pro Thr Tyr Gln Tyr Asn Met Asn Phe
    50                  55                  60

Glu Lys Leu Gly Lys Cys Ile Ile Asn Asn Lys Asn Phe Asp Lys
65                  70                  75                  80

Val Thr Gly Met Gly Val Arg Asn Gly Thr Asp Lys Asp Ala Glu Ala
                85                  90                  95

Leu Phe Lys Cys Phe Arg Ser Leu Gly Phe Asp Val Ile Val Tyr Asn
            100                 105                 110

Asp Cys Ser Cys Ala Lys Met Gln Asp Leu Leu Lys Lys Ala Ser Glu
        115                 120                 125

Glu Asp His Thr Asn Ala Ala Cys Phe Ala Cys Ile Leu Leu Ser His
    130                 135                 140

Gly Glu Glu Asn Val Ile Tyr Gly Lys Asp Gly Val Thr Pro Ile Lys
145                 150                 155                 160

Asp Leu Thr Ala His Phe Arg Gly Asp Arg Cys Lys Thr Leu Leu Glu
                165                 170                 175

Lys Pro Lys Leu Phe Phe Ile Gln Ala Cys Arg Gly Thr Glu Leu Asp
            180                 185                 190

Asp Ala Ile Gln Ala Asp Ser Gly Pro Ile Asn Asp Thr Asp Ala Asn
        195                 200                 205

Pro Arg Tyr Lys Ile Pro Val Glu Ala Asp Phe Leu Phe Ala Tyr Ser
    210                 215                 220

Thr Val Pro Gly Tyr Tyr Ser Trp Arg Ser Pro Gly Arg Gly Ser Trp
225                 230                 235                 240

Phe Val Gln Ala Leu Cys Ser Ile Leu Glu Glu His Gly Lys Asp Leu
                245                 250                 255
```

-continued

```
Glu Ile Met Gln Ile Leu Thr Arg Val Asn Asp Arg Val Ala Arg His
            260                 265                 270

Phe Glu Ser Gln Ser Asp Asp Pro His Phe His Glu Lys Lys Gln Ile
        275                 280                 285

Pro Cys Val Val Ser Met Leu Thr Lys Glu Leu Tyr Phe Ser Gln
    290                 295                 300

<210> SEQ ID NO 3
<211> LENGTH: 1159
<212> TYPE: DNA
<213> ORGANISM: Homo sapiens

<400> SEQUENCE: 3
gcacgagcgg atgggtgcta ttgtgaggcg gttgtagaag agtttcgtga gtgctcgcag      60
ctcatacctg tggctgtgta tccgtggcca cagctggttg gcgtcgcctt gaaatcccag    120
gccgtgagga gttagcgagc cctgctcaca ctcggcgctc tggttttcgg tgggtgtgcc    180
ctgcacctgc ctcttcccgc attctcatta taaaggtat ccatggagaa cactgaaaac    240
tcagtggatt caaatccat taaaatttg aaccaaaga tcatacatgg aagcgaatca    300
atggactctg gaatatccct ggacaacagt tataaatgg attatcctga tgggttta    360 tgtataataa ttaataataa gaattttcat aaaagcactg gaatgacatc tcggtctggt    420
acagatgtcg atgcagcaaa cctcagggaa acattcagaa acttgaaata tgaagtcagg    480
aataaaaatg atcttacacg tgaagaaatt gtggaattga tgcgtgatgt ttctaaagaa    540
gatcacagca aaggagcag ttttgtttgt gtgcttctga gccatggtga agaaggaata    600
atttttggaa caaatggacc tgttgacctg aaaaaaataa caaactttt cagaggggat    660 cgttgtagaa gtctaactgg aaaacccaaa cttttcatta ttcaggcctg ccgtggtaca    720
gaactggact gtggcattga cagacagt ggtgttgatg atgacatggc gtgtcataaa    780
ataccagtgg aggccgactt cttgtatgca tactccacag cacctggtta ttattcttgg    840
cgaaattcaa aggatggctc ctggttcatc cagtcgcttt gtgccatgct gaaacagtat    900
gccgacaagc ttgaattat gcacattctt acccgggtta accgaaaggt ggcaacagaa    960
tttgagtcct tttccttga cgctacttt catgcaaaga aacagattcc atgtattgtt   1020
tccatgctca caaaagaact ctatttttat cactaaagaa atggttggtt ggtggttttt   1080 tttagttgt atgccaagtg agaagatggt atatttgggt actgtatttc cctctcattg   1140
gggacctact ctcatgctg                                                1159

<210> SEQ ID NO 4
<211> LENGTH: 277
<212> TYPE: PRT
<213> ORGANISM: Homo sapiens

<400> SEQUENCE: 4

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
```

|   |   |   |   |   |   |   |   |   |   |   |
|---|---|---|---|---|---|---|---|---|---|---|
| 65 |   |   |   |   | 70 |   |   |   |   | 75 |   |   |   |   | 80 |

Leu Lys Tyr Glu Val Arg Asn Lys Asn Asp Leu Thr Arg Glu Glu Ile
                85                      90                      95

Val Glu Leu Met Arg Asp Val Ser Lys Glu Asp His Ser Lys Arg Ser
            100                     105                     110

Ser Phe Val Cys Val Leu Leu Ser His Gly Glu Glu Gly Ile Ile Phe
        115                     120                     125

Gly Thr Asn Gly Pro Val Asp Leu Lys Lys Ile Thr Asn Phe Phe Arg
    130                     135                     140

Gly Asp Arg Cys Arg Ser Leu Thr Gly Lys Pro Lys Leu Phe Ile Ile
145                 150                     155                     160

Gln Ala Cys Arg Gly Thr Glu Leu Asp Cys Gly Ile Glu Thr Asp Ser
                165                     170                     175

Gly Val Asp Asp Asp Met Ala Cys His Lys Ile Pro Val Glu Ala Asp
            180                     185                     190

Phe Leu Tyr Ala Tyr Ser Thr Ala Pro Gly Tyr Tyr Ser Trp Arg Asn
        195                     200                     205

Ser Lys Asp Gly Ser Trp Phe Ile Gln Ser Leu Cys Ala Met Leu Lys
    210                     215                     220

Gln Tyr Ala Asp Lys Leu Glu Phe Met His Ile Leu Thr Arg Val Asn
225                     230                     235                     240

Arg Lys Val Ala Thr Glu Phe Glu Ser Phe Ser Phe Asp Ala Thr Phe
                245                     250                     255

His Ala Lys Lys Gln Ile Pro Cys Ile Val Ser Met Leu Thr Lys Glu
            260                     265                     270

Leu Tyr Phe Tyr His
        275

<210> SEQ ID NO 5
<211> LENGTH: 31
<212> TYPE: DNA
<213> ORGANISM: Artificial sequence
<220> FEATURE:
<223> OTHER INFORMATION: Contains a Bam HI restriction enzyme site
     (underlined) followed by 18 nucleotides of ICE-LAP-3 coding
     sequence starting from the presumed terminal amino acid of the
     processed protein codon

<400> SEQUENCE: 5
gatcggatcc atgcgtgcgg ggacacgggt c                                31

<210> SEQ ID NO 6
<211> LENGTH: 31
<212> TYPE: DNA
<213> ORGANISM: Artificial sequence
<220> FEATURE:
<223> OTHER INFORMATION: Contains complementary sequences to an Xba I
     site followed by 21 nucleotides of ICE-LAP-3

<400> SEQUENCE: 6
gtactctaga tcattcaccc tggtggagga t                                31

<210> SEQ ID NO 7
<211> LENGTH: 31
<212> TYPE: DNA
<213> ORGANISM: Artificial sequence
<220> FEATURE:
<223> OTHER INFORMATION: Contains a Bam HI restriction enzyme site
     followed by 18 nucleotides of ICE-LAP-4 coding sequence starting
     from the presumed terminal amino acid of the processed protein
     codon

<400> SEQUENCE: 7
gatcggatcc atggagaaca ctgaaaactc a                              31

<210> SEQ ID NO 8
<211> LENGTH: 31
<212> TYPE: DNA
<213> ORGANISM: Artificial sequence
<220> FEATURE:
<223> OTHER INFORMATION: Contains complementary sequences to an Xba I
      site followed by 21 nucleotides of ICE-LAP-4

<400> SEQUENCE: 8
gtactctaga ttagtgataa aaatagagtt c                              31

<210> SEQ ID NO 9
<211> LENGTH: 22
<212> TYPE: DNA
<213> ORGANISM: Artificial sequence
<220> FEATURE:
<223> OTHER INFORMATION: Contains the ICE-LAP-3 translational initiation
      site ATG followed by 5 nucleotides of ICE-LAP-3 coding sequence
      starting from the initiation codon

<400> SEQUENCE: 9
gactatgcgt gcggggacac gg                                        22

<210> SEQ ID NO 10
<211> LENGTH: 53
<212> TYPE: DNA
<213> ORGANISM: Artificial sequence
<220> FEATURE:
<223> OTHER INFORMATION: Contains translation stop codon, HA tag and the
      last 21 nucleotides of the ICE-LAP-3 coding sequence, not
      including the stop codon

<400> SEQUENCE: 10
aatcaagcgt agtctgggac gtcgtatggg tattcaccct ggtggaggat ttg       53

<210> SEQ ID NO 11
<211> LENGTH: 21
<212> TYPE: DNA
<213> ORGANISM: Artificial sequence
<220> FEATURE:
<223> OTHER INFORMATION: Contains the ICE-LAP-4 translational initiation
      site, ATG, followed by 15 nucleotides of ICE-LAP-4 coding sequence
      starting from the initiation codon

<400> SEQUENCE: 11
accatggaga acactgaaaa c                                         21

<210> SEQ ID NO 12
<211> LENGTH: 53
<212> TYPE: DNA
<213> ORGANISM: Artificial sequence
<220> FEATURE:
<223> OTHER INFORMATION: Contains translation stop codon, HA tag and the
      last 21 nucleotides of the ICE-LAP-4 coding sequence, not
      including the stop codon

<400> SEQUENCE: 12
aatcaagcgt agtctgggac gtcgtatggg tagtgataaa aatagagttc ttt       53

<210> SEQ ID NO 13
<211> LENGTH: 503
<212> TYPE: PRT
<213> ORGANISM: Caenorhabditis elegans

<400> SEQUENCE: 13

```
Met Met Arg Gln Asp Arg Arg Ser Leu Leu Glu Arg Asn Ile Met Met
1               5                   10                  15

Phe Ser Ser His Leu Lys Val Asp Glu Ile Leu Glu Val Leu Ile Ala
            20                  25                  30

Lys Gln Val Leu Asn Ser Asp Asn Gly Asp Met Ile Asn Ser Cys Gly
            35                  40                  45

Thr Val Arg Glu Lys Arg Arg Glu Ile Val Lys Ala Val Gln Arg Arg
    50                  55                  60

Gly Asp Val Ala Phe Asp Ala Phe Tyr Asp Ala Leu Arg Ser Thr Gly
65                  70                  75                  80

His Glu Gly Leu Ala Glu Val Leu Glu Pro Leu Ala Arg Ser Val Asp
                85                  90                  95

Ser Asn Ala Val Glu Phe Glu Cys Pro Met Ser Pro Ala Ser His Arg
            100                 105                 110

Arg Ser Arg Ala Leu Ser Pro Ala Gly Tyr Thr Ser Pro Thr Arg Val
            115                 120                 125

His Arg Asp Ser Val Ser Val Ser Ser Phe Thr Ser Tyr Gln Asp
            130                 135                 140

Ile Tyr Ser Arg Ala Arg Ser Arg Ser Arg Ala Leu His Ser
145                 150                 155                 160

Ser Asp Arg His Asn Tyr Ser Pro Pro Val Asn Ala Phe Pro Ser
                165                 170                 175

Gln Pro Ser Ser Ala Asn Ser Ser Phe Thr Gly Cys Ser Ser Leu Gly
            180                 185                 190

Tyr Ser Ser Arg Asn Arg Ser Phe Ser Lys Ala Ser Gly Pro Thr
            195                 200                 205

Gln Tyr Ile Phe His Glu Glu Asp Met Asn Phe Val Asp Ala Pro Thr
    210                 215                 220

Ile Ser Arg Val Phe Asp Glu Lys Thr Met Tyr Arg Asn Phe Ser Ser
225                 230                 235                 240

Pro Arg Gly Met Cys Leu Ile Ile Asn Asn Glu His Phe Glu Gln Met
                245                 250                 255

Pro Thr Arg Asn Gly Thr Lys Ala Asp Lys Asp Asn Leu Thr Asn Leu
            260                 265                 270

Phe Arg Cys Met Gly Tyr Thr Val Ile Cys Lys Asp Asn Leu Thr Gly
            275                 280                 285

Arg Gly Met Leu Leu Thr Ile Arg Asp Phe Ala Lys His Glu Ser His
    290                 295                 300

Gly Asp Ser Ala Ile Leu Val Ile Leu Ser His Gly Glu Glu Asn Val
305                 310                 315                 320

Ile Ile Gly Val Asp Asp Ile Pro Ile Ser Thr His Glu Ile Tyr Asp
                325                 330                 335

Leu Leu Asn Ala Ala Asn Ala Pro Arg Leu Ala Asn Lys Pro Lys Ile
            340                 345                 350

Val Phe Val Gln Ala Cys Arg Gly Glu Arg Arg Asp Asn Gly Phe Pro
            355                 360                 365

Val Leu Asp Ser Val Asp Gly Val Pro Ala Phe Leu Arg Arg Gly Trp
    370                 375                 380

Asp Asn Arg Asp Gly Pro Leu Phe Asn Phe Leu Gly Cys Val Arg Pro
385                 390                 395                 400

Gln Val Gln Gln Val Trp Arg Lys Lys Pro Ser Gln Ala Asp Ile Leu
```

```
                    405                 410                 415
Ile Ala Tyr Ala Thr Thr Ala Gln Tyr Val Ser Trp Arg Asn Ser Ala
            420                 425                 430

Arg Gly Ser Trp Phe Ile Gln Ala Val Cys Glu Val Phe Ser Thr His
        435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Phe Trp Pro
            485                 490                 495

Glu Ala Arg Asn Ser Ala Val
            500

<210> SEQ ID NO 14
<211> LENGTH: 404
<212> TYPE: PRT
<213> ORGANISM: Homo sapiens

<400> SEQUENCE: 14

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
            85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
            165                 170                 175

Pro Arg Arg Thr Gly Ala Glu Val Asp Ile Thr Gly Met Thr Met Leu
            180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
            245                 250                 255

Gln Leu Asn Ala Ile Phe Asn Met Leu Asn Thr Lys Asn Cys Pro Ser
            260                 265                 270
```

-continued

```
Leu Lys Asp Lys Pro Lys Val Ile Ile Ile Gln Ala Cys Arg Gly Asp
        275                 280                 285

Ser Pro Gly Val Val Trp Phe Lys Asp Ser Val Gly Val Ser Gly Asn
        290                 295                 300

Leu Ser Leu Pro Thr Thr Glu Glu Phe Glu Asp Asp Ala Ile Lys Lys
305                     310                 315                 320

Ala His Ile Glu Lys Asp Phe Ile Ala Phe Cys Ser Ser Thr Pro Asp
                    325                 330                 335

Asn Val Ser Trp Arg His Pro Thr Met Gly Ser Val Phe Ile Gly Arg
                340                 345                 350

Leu Ile Glu His Met Gln Glu Tyr Ala Cys Ser Cys Asp Val Glu Glu
            355                 360                 365

Ile Phe Arg Lys Val Arg Phe Ser Phe Glu Gln Pro Asp Gly Arg Ala
            370                 375                 380

Gln Met Pro Thr Thr Glu Arg Val Thr Leu Thr Arg Cys Phe Tyr Leu
385                     390                 395                 400

Phe Pro Gly His
```

IMMUNOASSAY METHODS FOR DETECTING INTERLEUKIN-1 β CONVERTING ENZYME LIKE APOPTOSIS PROTEASE-3

This application is a divisional of application Ser. No. 09/613,508, filed Jul. 10, 2000 (now U.S. Pat. No. 6,835,555, issued Dec. 28, 2004), which is a divisional of application Ser. No. 08/462,969, filed Jun. 5, 1995 (now U.S. Pat. No. 6,087,150, issued Jul. 11, 2000), which is a continuation-in-part of application Ser. No. 08/334,251, filed Nov. 1, 1994 (now U.S. Pat. No. 6,538,121, issued Mar. 25, 2003), each of which is hereby incorporated by reference in its entirety.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are interleukin-1 β converting enzyme like apoptosis protease-3 and interleukin-1 β converting enzyme like apoptosis protease-4, sometimes hereinafter referred to collectively as "ICE-LAP-3 and 4". The invention also relates to inhibiting the action of such polypeptides.

It has recently been discovered that an interleukin-1 β converting enzyme (ICE) is responsible for cleaving pro-IL-1 β into mature and active IL-1 β and is also responsible for programmed cell death (or apoptosis), which is a process through which organisms get rid of unwanted cells. The present invention is directed to ICE-LAP-3 and 4 which are structurally related to ICE.

In the nematode *caenorhabditis elegans*, a genetic pathway of programmed cell death has been identified (Ellis, R. E., et al. Annu. Rev. Cell Biol., 7:663-698 (1991)). Two genes, ced-3 and ced-4, are essential for cells to undergo programmed cell death in *C. elegans* (Ellis, H. M., and Horvitz, H. R., Cell, 44:817-829 (1986)). Recessive mutations that eliminate the function of these two genes prevent normal programmed cell death during the development of *C. elegans*. The known vertebrate counterpart to ced-3 protein is ICE. The overall amino acid identity between ced-3 and ICE is 28%, with a region of 115 amino acids (residues 246-360 of ced-3 (SEQ ID NO:13) and 164-278 of ICE (SEQ ID NO:14)) that shows the highest identity (43%). This region contains a conserved pentapeptide, QACRG (residues 356-360 of ced-3 (SEQ ID NO:13)), which contains a cysteine known to be essential for ICE function. The ICE-LAP-1 and 2 polypeptides of the present invention also have the same conserved pentapeptide and the cysteine residue which is essential for ICE function.

The similarity between ced-3 and ICE suggests not only that ced-3 might function as a cysteine protease but also that ICE might act as a vertebrate programmed cell death gene. ced-3 and the vertebrate counterpart, ICE, control programmed cell death during embryonic development, (Gagliarnini, V. et al., Science, 263:826:828 (1994).

ICE mRNA has been detected in a variety of tissues, including peripheral blood monocytes, peripheral blood lymphocytes, peripheral blood neutrophils, resting and activated peripheral blood T lymphocytes, placenta, the B lymphoblastoid line CB23, and monocytic leukemia cell line THP-1 cells (Cerretti, D.P., et al., Science, 256:97-100 (1992)), suggesting that ICE may have an additional substrate in addition to pro-IL-1. The substrate that ICE acts upon to cause cell death is presently unknown. One possibility is that it may be a vertebrate homolog of the *C. elegans* cell death gene ced-4. Alternatively, ICE might directly cause cell death by proteolytically cleaving proteins that are essential for cell viability.

The mammalian gene bcl-2, has been found to protect immune cells called lymphocytes from cell suicide. Also, crmA, a cow pox virus gene protein product inhibits ICE's protein splitting activity.

In accordance with one aspect of the present invention, there is provided novel mature polypeptides, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there are provided processes for producing such polypeptides by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptides, or polynucleotide encoding such polypeptides for therapeutic purposes, for example, as an antiviral agent, an anti-tumor agent and to control embryonic development and tissue homeostasis.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of Alzheimer's disease, Parkinson's disease, rheumatoid arthritis, septic shock and head injury.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A-B show the cDNA sequence (SEQ ID NO:1) and corresponding deduced amino acid sequence of ICE-LAP-3. The polypeptide encoded by the amino acid sequence (SEQ ID NO:2) shown is the putative mature form of the polypeptide (minus the initial methionine residue), and the standard one-letter abbreviation for amino acids is used.

FIGS. 2A-B show the cDNA sequence (SEQ ID NO:3) and corresponding deduced amino acid sequence (SEQ ID NO:4) of ICE-LAP-4. The polypeptide encoded by the amino acid sequence shown is the putative mature form of the polypeptide (minus the initial methionine residue).

FIGS. 3A-C show an amino acid sequence comparison between ICE-LAP-3 (SEQ ID NO:2), ICE-LAP-4 (SEQ ID NO:4), human ICE (SEQ ID NO:14) and the C. elegans cell death gene ced-3 (SEQ ID NO: 13). Shaded areas represent amino acid matches between the different sequences.

Figure 3A:
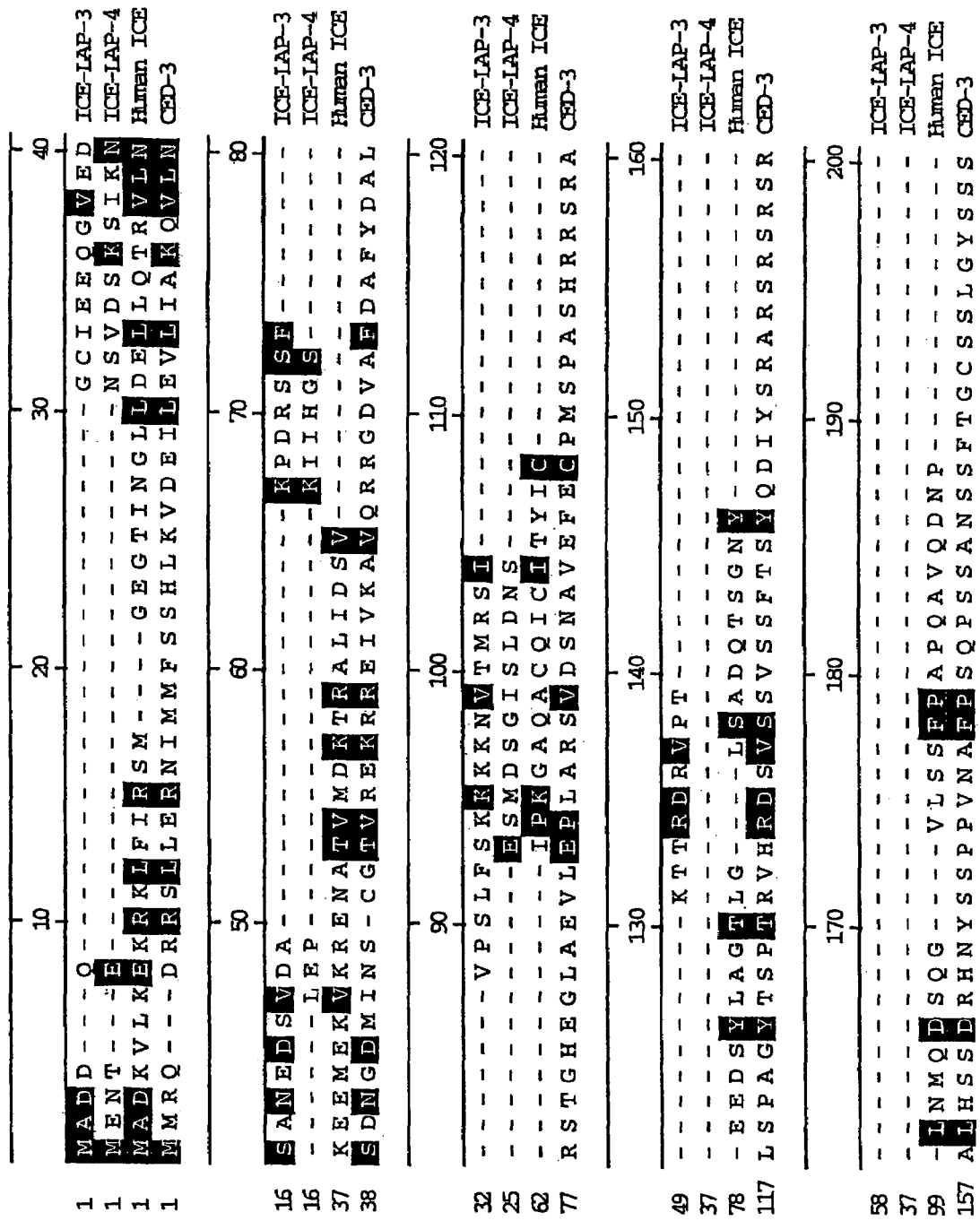

In accordance with an aspect of the present invention, there are provided isolated nucleic acids (polynucleotides) which encode the mature polypeptides having the deduced amino acid sequence of FIGS. 1A-B and 2A-B (SEQ ID NO:2 and 4, respectively) or for the mature polypeptide encoded by the cDNA of the clones deposited as ATCC Deposit No. 75875 and 75873. ATCC Deposit No. 75875 contains the cDNA encoding for ICE-LAP-3, and ATCC Deposit No. 75873 contains the cDNA encoding for ICE-LAP-4. The deposit was made Aug. 25, 1994. These deposits are biological deposits with the American Type Culture Collection ("ATCC") located at 10801 University Boulevard, Manassas, Va. 20110-2209. Since the deposits referred to are being maintained under the terms of the Budapest Treaty, they will be made available to a patent office signatory to the Budapest Treaty.

The polynucleotide encoding ICE-LAP-3 can be detected from human prostate, human endometrial tumor, human pancreatic tumor, human adrenal gland tumor and human tonsil. The full-length encoding ICE-LAP-3 was discovered in a cDNA library derived from human endometrial tumor. It is structurally related to the Interleukin-1 converting enzyme family. It contains an open reading frame encoding a protein of approximately 341 amino acid residues. The protein exhibits the highest degree of homology to C. elegans cell death gene ced-3 which is a homolog of human interleukin-1 converting enzyme, with 68% similarity and 43% identity over the entire amino acid sequence. It should be pointed out that the pentapeptide QACRG is conserved and is located at amino acid position 184-188 of the sequence shown in SEQ ID NO:2.

The polynucleotide encoding ICE-LAP-4 was discovered in a cDNA library derived from human tonsils. It is structurally related to the ICE family. It contains an open reading frame encoding a protein of about 277 amino acid residues. The protein exhibits the highest degree of homology to the C. elegans cell death gene ced-3 with 29% identity and 46% similarity over a 277 amino acid stretch. It is also important that the pentapeptide QACRG is conserved and is located at amino position 161-165 of the sequence shown in SEQ ID NO:4.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encode the mature polypeptides may be identical to the coding sequence shown in FIGS. 1A-B and 2A-B (SEQ ID NO:1 and 3) or that of the deposited clones or may be a different coding sequence which coding sequence, as a result of the redundancy or degeneracy of the genetic code, encode the same mature polypeptides, and derivatives thereof, as the DNA of FIGS. 1A-B and 2A-B (SEQ ID NO:1 and 3) or the deposited cDNA.

The polynucleotides which encode for the mature polypeptides of FIGS. 1A-B and 2A-B (SEQ ID NO:2 and 4) or for the mature polypeptides encoded by the deposited cDNAs may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequence of FIGS. 1A-B and 2A-B (SEQ ID NO:2 and 4) or the polypeptides encoded by the cDNA of the deposited clones. The variants of the polynucleotides may be naturally occurring allelic variants of the polynucleotides or non-naturally occurring variants of the polynucleotides.

Thus, the present invention includes polynucleotides encoding the same mature polypeptides as shown in FIGS. 1A-B and 2A-B (SEQ ID NO:2 and 4) or the same mature polypeptides encoded by the cDNA of the deposited clones as well as variants of such polynucleotides which variants encode for a fragment, derivative or analog of the polypeptides of FIGS. 1A-B and 2A-B (SEQ ID NO:2 and 4) or the polypeptides encoded by the cDNA of the deposited clones. Such nucleotide variants include deletion variants, substitution variants and addition or insertion variants.

As hereinabove indicated, the polynucleotides may have a coding sequence which is a naturally occurring allelic variant of the coding sequence shown in FIGS. 1A-B and 2A-B (SEQ ID NO:1 and 3) or of the coding sequence of the deposited clones. As known in the art, an allelic variant is an alternate form of a polynucleotide sequence which may have a substitution, deletion or addition of nucleotides, which does not substantially alter the function of the encoded polypeptides. The polynucleotides may also encode for a proprotein which is the mature protein plus additional 5' amino acid residues.

The polynucleotides of the present invention may also have the coding sequence fused in frame to a sequence which allows for purification of the polypeptide of the present invention. The marker sequence may be a hexa-histidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length genes of the present invention may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A-B and 2A-B (SEQ ID NO:1 and 3) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1 and 3, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and 4 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to ICE-LAP-3 and 4 polypeptides which have the deduced amino acid sequence of FIGS. 1A-B and 2A-B (SEQ ID NO:2 and 4) or which has the amino acid sequence encoded by the deposited cDNAs, as well as fragments, analogs and derivatives of such polypeptides.

The terms "fragment," "derivative" and "analog" when referring to the polypeptides of FIGS. 1A-B and 2A-B (SEQ ID NO:2 and 4) or that encoded by the deposited cDNA, means polypeptides which retain essentially the same biological function or activity as such polypeptides, and wherein derivatives include polypeptides with enhanced or reduced biological function.

The polypeptides of the present invention may be recombinant polypeptides, natural polypeptides or synthetic polypeptides, preferably recombinant polypeptides.

The fragment, derivative or analog of the polypeptides of FIGS. 1A-B and 2A-B (SEQ ID NO:2 and 4) or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 and 4 (in particular the mature polypeptide) as well as polypeptides which have at least 70% similarity (preferably at least a 70% identity) to the polypeptide of SEQ ID NO:2 and 4 and more preferably at least a 90% similarity (more preferably at least a 90% identity) to the polypeptide of SEQ ID NO:2 and 4 and still more preferably at least a 95% similarity (still more preferably at least a 95% identity) to the polypeptide of SEQ ID NO:2 and 4 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the ICE-LAP-3 and 4 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTRs from retroviruses, e.g. RSV, HIV, HTLVI, CMV or SV40 promoter, the E. coli. lac or trp, the phage lambda $P_L$ promoter and other promoters known to control expression of genes in prokaryotic or eukaryotic cells or their viruses. However, also cellular signals can be used, for example, human-β-actin-promoter). The expression vector can contain a ribosome binding site for translation initiation and a transcription terminator. The vector may also include appropriate sequences for amplifying the copy number of the gene.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Bacillus subtilis, Streptomyces, Salmonella typhimurium; fungal cells, such as yeast; insect cells such as Drosophila and Spodoptera Sf9; adenoviruses; animal cells such as CHO, COS, HEK 293 or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD 10, phagescript, psiX 174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, lipofection or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, polyadenylation site, splice donor and acceptor sites, transcriptional termination sequences, and 5' flanking nontranscribed sequences. DNA sequences derived from the SV40 splice and polyadenylation sites may be used to provide the required nontranscribed genetic elements.

The ICE-LAP-3 and 4 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The ICE-LAP-3 and 4 polypeptides may be employed to treat abnormally controlled programmed cell death. Abnormally controlled programmed cell death may be an underlying cause of cancers due to an abnormal amount of cell growth. Accordingly, since ICE-LAP genes are implicated in programmed cell death, they may be used to target unwanted cells, for example, cancerous cells. ICE-LAP-3 and 4 may also be used to control vertebrate development and tissue homeostasis, due to its apoptosis ability.

Also, ICE-LAP-3 and 4 polypeptides may be used to overcome many viral infections by overcoming the suppressed programmed cell death, since programmed cell death may be one of the primary antiviral defense mechanisms of cells.

ICE-LAP-3 and 4 may also be employed to treat immunosuppression related disorders, such as AIDS, by targeting virus infected cells for cell death.

The present invention is further related to a process of screening compounds to identify antagonists to the ICE-LAP-3 and 4 polypeptides of the present invention. An example of such an assay comprises combining ICE-LAP-3 or 4 and a potential antagonist compound with their natural substrate under conditions allowing for action upon the substrate and determining whether the compound prevents ICE-LAP-3 or 4 from cleaving the substrate.

Potential antagonists include an antibody, or in some cases, an oligopeptide, which binds to the polypeptide. Alternatively, a potential antagonist may be a closely related protein which binds to the substrate, however, they are inactive forms of the polypeptide and thereby prevent the action of the polypeptide of the present invention.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of ICE-LAP 3 and 4. The antisense RNA oligonucleotide hybridizes to the mRNA in vivo and blocks translation of the mRNA molecule into ICE-LAP 3 and 4 polypeptide (Antisense - Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of ICE-LAP 3 and 4.

Potential antagonists include a small molecule which binds to and occupies the catalytic site of the polypeptides thereby making the catalytic site inaccessible to substrate such that normal biological activity is prevented. Examples of small molecules include but are not limited to small peptides or peptide-like molecules.

The antagonists may be employed to treat The antagonists non-programmed necrotic cell death related to cardiovascular diseases, strokes, trauma, and other degenerative diseases where abnormal regulation of ICE-LAP 3 and 4 may lead to pathological cell death, for example, immunosuppression-related disorders, Alzheimer's disease, Parkinson's disease and rheumatoid arthritis.

The antagonists may also be employed to treat immune-based diseases of the lung and airways, central nervous system, eyes and ears, joints, bones, cardiovascular system and gastrointestinal and urogenital systems. The antagonists may be employed in a composition with a pharmaceutically acceptable carrier, e.g., as hereinafter described.

The polypeptides of the present invention and antagonist compounds may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or antagonists of the present invention may be employed in conjunction with other therapeutic compounds.

The pharmaceutical compositions may be administered in a convenient manner such as by the intravenous, intraperitoneal, intramuscular, subcutaneous, intranasal or intradermal routes. ICE-LAP-3 and 4 are administered in an amount which is effective for treating and/or prophylaxis of the specific indication. In general, ICE-LAP-3 and 4 will be administered in an amount of at least 10 µg/kg body weight, and in most cases they will be administered in an amount not in excess of 8 mg/Kg body weight per day. In most cases, the dosage is from about 10 µg/kg to about 1 mg/kg body weight daily, taking into account the routes of administration, symptoms, etc.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the genes of the present invention as a diagnostic. Detection of a mutated form of the genes will allow a diagnosis of a disease or a susceptibility to a disease which results from underexpression of the polypeptide of the present invention.

Individuals carrying mutations in the human ICE-LAP 3 and 4 gene may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163-166 (1986)) prior to analysis. RNA or cDNA may also be used for the same purpose. As an example, PCR primers complementary to the nucleic acid encoding a polypeptide of the present invention can be used to identify and analyze mutations. For example, deletions and insertions can be detected by a change in size of the amplified product in comparison to the normal genotype. Point mutations can be identified by hybridizing amplified DNA to radiolabeled ICE-LAP 3 and 4 RNA or alternatively, radiolabeled ICE-LAP 3 and 4 antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397-4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of ICE-LAP 3 and 4 protein in various tissues. Assays used to detect levels of ICE-LAP 3 and 4 protein in a sample derived from a host are well-known to those of skill in the art and include radioimmunoassays, competitive-binding assays, Western Blot analysis and preferably an ELISA assay. An ELISA assay initially comprises preparing an antibody specific to the ICE-LAP 3 and 4 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a nonspecific protein such as bovine serum albumin. Next, the monoclonal antibody is incubated in the dish during which time the monoclonal antibodies attach to any ICE-LAP 3 and 4 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to ICE-LAP 3 and 4. Unattached reporter antibody is then washed out. Peroxidase substrates are then added to the dish and the amount of color developed in a given time period is a measurement of the amount of ICE-LAP 3 and 4 protein present in a given volume of patient sample when compared against a standard curve.

A competition assay may be employed wherein antibodies specific to ICE-LAP 3 and 4 are attached to a solid support and labeled ICE-LAP 3 and 4 and a sample derived from the host are passed over the solid support and the amount of label detected attached to the solid support can be correlated to a quantity of ICE-LAP 3 and 4 in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37 C are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980), or agarose gels (0.5-1.5%).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456-457 (1973).

EXAMPLE 1

Bacterial Expression and Purification of ICE-LAP-3

The DNA sequence encoding ICE-LAP-3, ATCC # 75875, is initially amplified using PCR oligonucleotide primers corresponding to the 5' sequences of the processed ICE-LAP-3 protein (minus the signal peptide sequence) and the vector sequences 3' to the ICE-LAP-3 gene. Additional nucleotides corresponding to ICE-LAP-3 are added to the 5' and 3' sequences respectively. The 5' oligonucleotide primer has the sequence 5' GATC<u>GGATCC</u>ATGCGTGCGGGGACACGGGTC 3' (SEQ ID NO:5)

contains a Bam HI restriction enzyme site (underlined) followed by 18 nucleotides of ICE-LAP-3 coding sequence starting from the presumed terminal amino acid of the processed protein codon. The 3' sequence (SEQ ID NO:6)
5' GTAC<u>TCTAGA</u>TCATTCACCCTGGTGGAGGAT 3' contains complementary sequences to an Xba I site (underlined) followed by 21 nucleotides of ICE-LAP-3. The restriction enzyme sites correspond to the restriction enzyme sites on the bacterial expression vector pQE-9 (Qiagen, Inc. 9259 Eton Avenue, Chatsworth, Calif, 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Bam HI and Xba I. The amplified sequences are ligated into pQE-9 and are inserted in frame with the sequence encoding for the histidine tag and the RBS. The ligation mixture is then used to transform E. coli available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized ICE-LAP-3 is purified from this solution by chromatography on a Nickel-Chelate column under conditions that allow for tight binding by proteins containing the 6-His tag (Hochuli, E. et al., J. Chromatography 411:177-184 (1984)). ICE-LAP-3 (95% pure is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 2

Bacterial Expression and Purification of ICE-LAP-4

The DNA sequence encoding ICE-LAP-4, ATCC # 75873, is initially amplified using PCR oligonucleotide primers corresponding to the 5' sequences of the processed ICE-LAP-4 protein (minus the signal peptide sequence) and the vector sequences 3' to the ICE-LAP-4 gene. Additional nucleotides corresponding to ICE-LAP-4 are added to the 5' and 3' sequences respectively. The 5' oligonucleotide primer has the sequence 5' GATC<u>GGATCC</u>ATGGAGAACACTGAAAACTCA 3' (SEQ ID NO:7)

contains a Bam HI restriction enzyme site (underlined) followed by 18 nucleotides of ICE-LAP-4 coding sequence starting from the presumed terminal amino acid of the processed protein codon. The 3' sequence (SEQ D NO:8)
5' GTAC<u>TCTAGA</u>TTAGTGATAAAAATAGAGTTC 3' contains complementary sequences to an Xba I site (underlined) followed by 21 nucleotides of ICE-LAP-4. The restriction enzyme sites correspond to the restriction enzyme sites on the bacterial expression vector pQE-9 (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Bam HI and Xba I. The amplified sequences are ligated into pQE-9 and are inserted in frame with the sequence encoding for the histidine tag and the RBS. The ligation mixture is then used to transform E. coli available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized ICE-LAP-4 is purified from this solution by chromatography on a Nickel-Chelate column under conditions that allow for tight binding by proteins containing the 6-His tag (Hochuli, E. et al., J. Chromatography 411:177-184 (1984)). ICE-LAP-4 (95% pure is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

EXAMPLE 3

Expression of Recombinant ICE-LAP-3 in COS Cells

The expression of a plasmid, ICE-LAP-3 HA, is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire ICE-LAP-3 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:
The DNA sequence encoding for ICE-LAP-3, ATCC # 75875, was constructed by PCR on the full-length ICE-LAP-3 using two primers: the 5' primer

5' GACTATGCGTGCGGGACACGG 3' (SEQ ID NO:9)

contains the ICE-LAP-3 translational initiation site ATG followed by 5 nucleotides of ICE-LAP-3 coding sequence starting from the initiation codon; the 3' sequence

5' AATCAAGCGTAGTCTGGGACGTCGTATGGGTATTCACCCTGGTGGAG

GATTTG 3' (SEQ ID NO:10)

contains translation stop codon, HA tag and the last 21 nucleotides of the ICE-LAP-3 coding sequence (not including the stop codon). Therefore, the PCR product contains the ICE-LAP-3 coding sequence followed by HA tag fused in frame, and a translation termination stop codon next to the HA tag. The PCR amplified DNA fragment was ligated with pcDNAI/Amp by blunt end ligation. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ICE-LAP-3, COS cells were transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the ICE-LAP-3 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 OmM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 4

Expression of Recombinant ICE-LAP-4 in COS Cells

The expression of a plasmid, ICE-LAP-4 HA, is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire ICE-LAP-4 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lemer, 1984, Cell 37, 767). The infusion of HA tag to our target protein allows easy detection of the recombinant protein with an antibody that recognizes the HA epitope.

The plasmid construction strategy is described as follows:

The DNA sequence encoding for ICE-LAP-4, ATCC # 75873, was constructed by PCR on the full-length ICE-LAP-4 using two primers: the 5' primer

```
5' ACCATGGAGAACACTGAAAAC 3' (SEQ ID NO:11)
``` contains the ICE-LAP-4 translational initiation site, ATG, followed by 15 nucleotides of ICE-LAP-4 coding sequence starting from the initiation codon; the 3' sequence

```
5' AATCAAGCGTAGTCTGGGACGTCGTATGGGTAGTGATAAAAATAGAGTTCTTT 3' (SEQ ID NO:12)
``` contains translation stop codon, HA tag and the last 21 nucleotides of the ICE-LAP-4 coding sequence (not including the stop codon). Therefore, the PCR product contains the ICE-LAP-4 coding sequence followed by HA tag fused in frame, and a translation termination stop codon next to the HA tag. The PCR amplified DNA fragment was ligated with pcDNAI/Amp by blunt end ligation. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant ICE-LAP-4, COS cells were transfected with the expression vector by the DEAE-DEXTRAN method (J. Sambrook, E. Fritsch, T. Maniatis, Molecular Cloning: A Laboratory Manual, Cold Spring Laboratory Press, (1989)). The expression of the ICE-LAP-4 HA protein was detected by radiolabelling and immunoprecipitation method (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 5OmM Tris, pH 7.5) (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 5

Expression Pattern of ICE-LAP-3 in Human Tissue

Northern blot analysis was carried out to examine the levels of expression of ICE-LAP-3 in human tissues. Total cellular RNA samples were isolated with RNAzol B system (Biotecx Laboratories, Inc. 6023 South Loop East, Houston, Tex. 77033). About 10 g of total RNA isolated from each human tissue specified was separated on 1% agarose gel and blotted onto a nylon filter (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime -3 Prime, Inc. 5603 Arapahoe Road, Boulder, Colo. 80303). The filter was then hybridized with radioactive labeled full length ICE-LAP-3 gene at 1,000,000 cpm/ml in 0.5 M NaPO$_4$, pH 7.4 and 7% SDS overnight at 65 C. After wash twice at room temperature and twice at 60 C with 0.5×SSC, 0.1% SDS, the filter was then exposed at −70 C overnight with an intensifying screen. The message RNA for ICE-LAP-3 is abundant in liver.

EXAMPLE 6

Expression Pattern of ICE-LAP-4 in Human Tissue

Northern blot analysis is carried out to examine the levels of expression of ICE-LAP-4 in human tissues. Total cellular RNA samples were isolated with RNAzol B system (Biotecx Laboratories, Inc. 6023 South Loop East, Houston, Tex. 77033). About 10 g of total RNA isolated from each human tissue specified was separated on 1% agarose gel and blotted onto a nylon filter (Sambrook, Fritsch, and Maniatis, Molecular Cloning, Cold Spring Harbor Press, (1989)). The labeling reaction was done according to the Stratagene Prime-It kit with 50ng DNA fragment. The labeled DNA was purified with a Select-G-50 column. (5 Prime −3 Prime, Inc. 5603 Arapahoe Road, Boulder, Colo. 80303). The filter was then hybridized with radioactive labeled full length ICE-LAP-4 gene at 1,000,000 cpm/ml in 0.5 M NaPO$_4$, pH 7.4 and 7%

SDS overnight at 65 C. After wash twice at room temperature and twice at 60 C with 0.5×SSC, 0.1% SDS, the filter was then exposed at −70 C overnight with an intensifying screen.

EXAMPLE 7

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An immunoassay method, comprising:
    (a) contacting a sample with an antibody or fragment thereof that binds an ICE-LAP 3 polypeptide consisting of amino acid residues 1 to 303 of SEQ ID NO:2; and
    (b) detecting binding of said ICE-LAP 3 polypeptide in said sample to said antibody.

2. The immunoassay method of claim 1, wherein said assay is selected from the group consisting of a radioimmunoassay, a competitive-binding assay, a Western blot analysis and an ELISA assay.

3. The immunoassay method of claim 1, wherein said detecting step comprises generating a signal from a reporter antibody that binds said antibody or fragment thereof, wherein a detectable reagent is attached to said reporter antibody.

4. The immunoassay method of claim 3, wherein said detectable reagent is comprises a radiolabel, a fluorescent label, or an enzyme label.

5. The immunoassay method of claim 1, wherein said antibody is a monoclonal antibody.

6. The immunoassay method of claim 1, wherein said antibody is a polyclonal antibody.

7. The immunoassay method of claim 1, wherein said antibody is a chimeric antibody.

8. The immunoassay method of claim 5, wherein said antibody is a human antibody.

9. The immunoassay method of claim 1, wherein said antibody is a single chain antibody.

10. The immunoassay method of claim 1, wherein said antibody is an Fab fragment.

11. The immunoassay method of claim 1, further comprising comparing the results obtained from said detecting step to a standard curve to determine the amount of protein present in a given volume of said sample.

12. The immunoassay method of claim 1, wherein said sample is a tissue sample obtained from a patient.

* * * * *